United States Patent
Liau et al.

(10) Patent No.: US 11,844,705 B2
(45) Date of Patent: Dec. 19, 2023

(54) IMPLANT GUIDE SYSTEM FOR HIP REPLACEMENT SURGERY

(71) Applicants: United Orthopedic Corporation, Hsinchu (TW); China Medical University, Taichung (TW)

(72) Inventors: Jiann-Jong Liau, Hsinchu (TW); Chih-Hao Chang, Hsinchu (TW); Kui-Chou Huang, Hsinchu (TW); Yi-Wen Chen, Hsinchu (TW); Cheng-Ting Shih, Hsinchu (TW)

(73) Assignees: UNITED ORTHOPEDIC CORPORATION, Hsinchu (TW); CHINA MEDICAL UNIVERSITY, Taichung (TW)

( * ) Notice: Subject to any disclaimer, the term of this patent is extended or adjusted under 35 U.S.C. 154(b) by 198 days.

(21) Appl. No.: 17/496,134

(22) Filed: Oct. 7, 2021

(65) Prior Publication Data
US 2022/0125601 A1  Apr. 28, 2022

Related U.S. Application Data

(60) Provisional application No. 63/104,584, filed on Oct. 23, 2020.

(51) Int. Cl.
*A61F 2/46* (2006.01)
*A61F 2/34* (2006.01)
*A61F 2/30* (2006.01)

(52) U.S. Cl.
CPC .............. *A61F 2/4609* (2013.01); *A61F 2/34* (2013.01); *A61F 2002/30331* (2013.01)

(58) Field of Classification Search
CPC ............ A61B 17/1666; A61B 17/1742; A61B 17/1746; A61B 17/175; A61F 2/4607; A61F 2/4609
See application file for complete search history.

(56) References Cited

U.S. PATENT DOCUMENTS

| | | | | |
|---|---|---|---|---|
| 8,172,850 B2 * | 5/2012 | McMinn | ................ | A61B 17/15 606/91 |
| 9,101,378 B2 * | 8/2015 | Murphy | .................... | B43L 7/10 |
| 2004/0230199 A1 * | 11/2004 | Jansen | .................. | A61B 34/10 600/425 |
| 2005/0107799 A1 * | 5/2005 | Graf | ....................... | A61B 90/50 606/81 |
| 2008/0269757 A1 * | 10/2008 | McMinn | .............. | B23D 51/025 606/87 |

(Continued)

*Primary Examiner* — Anu Ramana
(74) *Attorney, Agent, or Firm* — Locke Lord LLP; Tim Tingkang Xia, Esq.

(57) ABSTRACT

An implant guide system for hip replacement surgery includes an angle guide member and a first positioning plate. The angle guide member has a body and a protrusion that are substantially connected to each other. The body has a curved surface corresponding in shape to a surface of a patient's acetabulum. The protrusion has a first through hole extending to the body. An acute angle is defined between an extension line of the first through hole and a flat surface of the body. The first positioning plate has a first holding portion and a first spacing portion that are substantially connected to each other. The first spacing portion has a second through hole, a third through hole and a fourth through hole that are parallel to each other.

10 Claims, 15 Drawing Sheets

(56) References Cited

U.S. PATENT DOCUMENTS

| | | | |
|---|---|---|---|
| 2009/0306679 A1* | 12/2009 | Murphy | B43L 7/10 606/130 |
| 2014/0135940 A1* | 5/2014 | Goldstein | A61B 17/15 623/22.21 |
| 2015/0012001 A1* | 1/2015 | Theiss | A61F 2/4609 606/87 |

\* cited by examiner

IMPLANT GUIDE SYSTEM FOR HIP REPLACEMENT SURGERY

CROSS-REFERENCE TO RELATED APPLICATION

This application claims the benefit of U.S. Provisional Patent Application No. 63/104,584, filed Oct. 23, 2020, which is incorporated by reference herein in its entirety.

FIELD OF THE INVENTION

The present invention relates to a surgical implant guide system, and more particularly to an implant guide system for hip replacement surgery.

BACKGROUND OF THE INVENTION

In general, when a patient undergoes hip replacement surgery, the positioning of the acetabular cup is one of the keys to the success of the operation. The inaccurate positioning of the acetabular cup often causes a series of problems after the operation.

Therefore, in order to accurately place the acetabular cup in the correct position in the acetabulum, it is required for an assistive device used for precise positioning in hip replacement surgery.

SUMMARY OF THE INVENTION

The primary object of the present invention is to provide an implant guide system for hip replacement surgery, comprising an angle guide member and a first positioning plate. The angle guide member has a body and a protrusion that are substantially connected to each other. The body has a curved surface corresponding in shape to a surface of a patient's acetabulum. The protrusion has a first through hole extending to the body. An acute angle is defined between an extension line of the first through hole and a flat surface of the body. The first positioning plate has a first holding portion and a first spacing portion that are substantially connected to each other. The first spacing portion has a second through hole, a third through hole and a fourth through hole that are parallel to each other. A first positioning rod is inserted through the first through hole and the second through hole. A second positioning rod is inserted through the third through hole and secured to a first positioning point near the acetabulum. A third positioning rod is inserted through the fourth through hole and secured to a second positioning point next to the first positioning point. The second positioning rod and the third positioning rod are arranged at the acute angle relative to the flat surface of the body so that an acetabular cup can be accurately coupled to the acetabulum.

Embodiments of the present invention will now be described, by way of example only, with reference to the accompanying drawings.

DETAILED DESCRIPTION OF THE PREFERRED EMBODIMENTS

In order to improve the accuracy of positioning an acetabular cup to a patient's acetabulum, the present invention provides an implant guide system for hip replacement surgery. A positioning plate and an angle guide member are first used for positioning, so that the subsequent steps of grinding the surface of the acetabulum and placing the acetabular cup to the acetabulum can be performed in the correct position.

FIG. 1, FIG. 2A, FIG. 2B, FIG. 3 and FIG. 4 illustrate the positioning plate and the angle guide member of the implant guide system for hip replacement surgery according to embodiments of the present invention.

Figure 1:
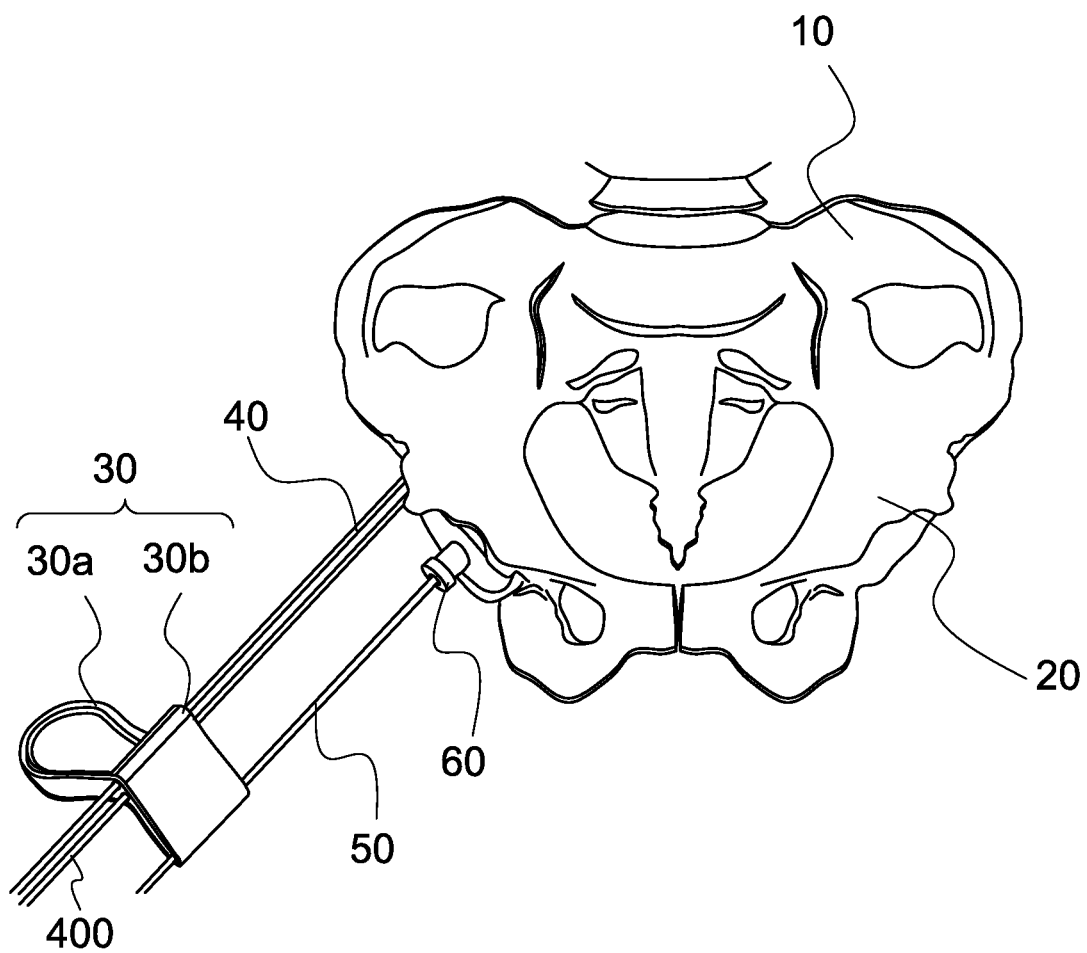
FIG. 1 shows some components of the implant guide system for hip replacement surgery according to an embodiment of the present invention.
Figure 2A:
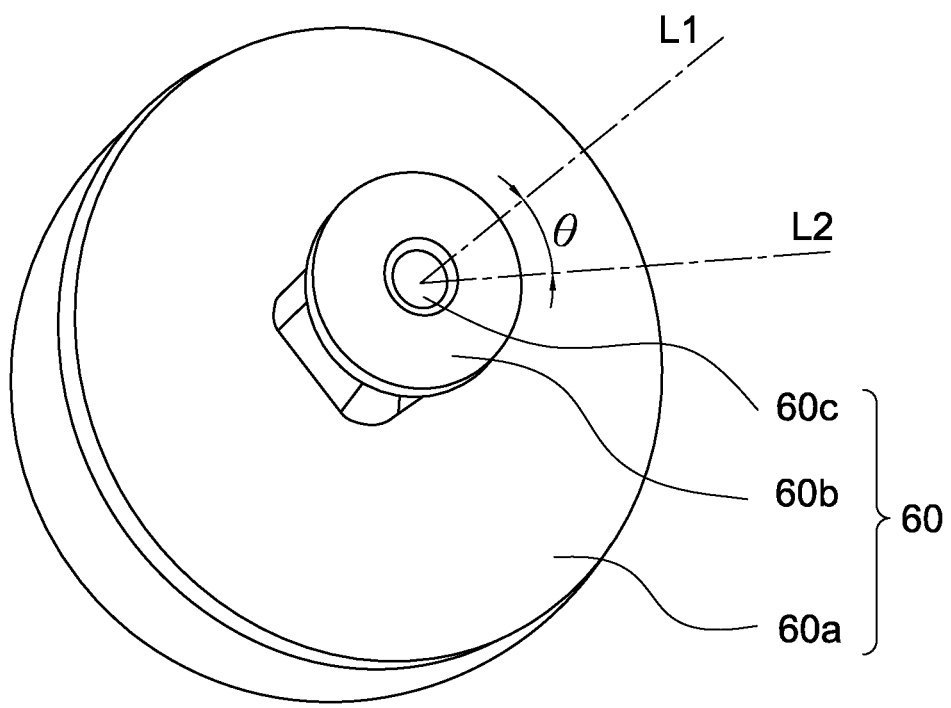
FIG. 2A shows the angle guide member according to an embodiment of the present invention.
Figure 2B:
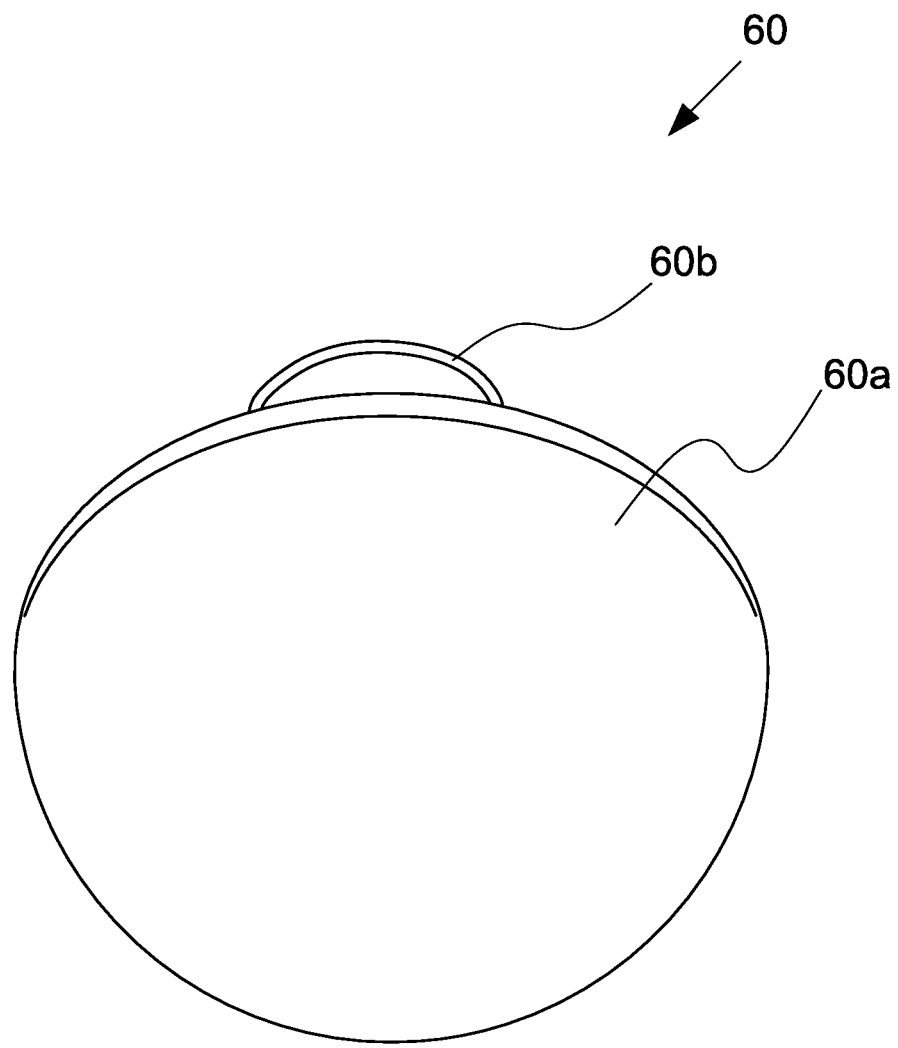
FIG. 2B shows the other side of the angle guide member of FIG. 2A.
Figure 3:
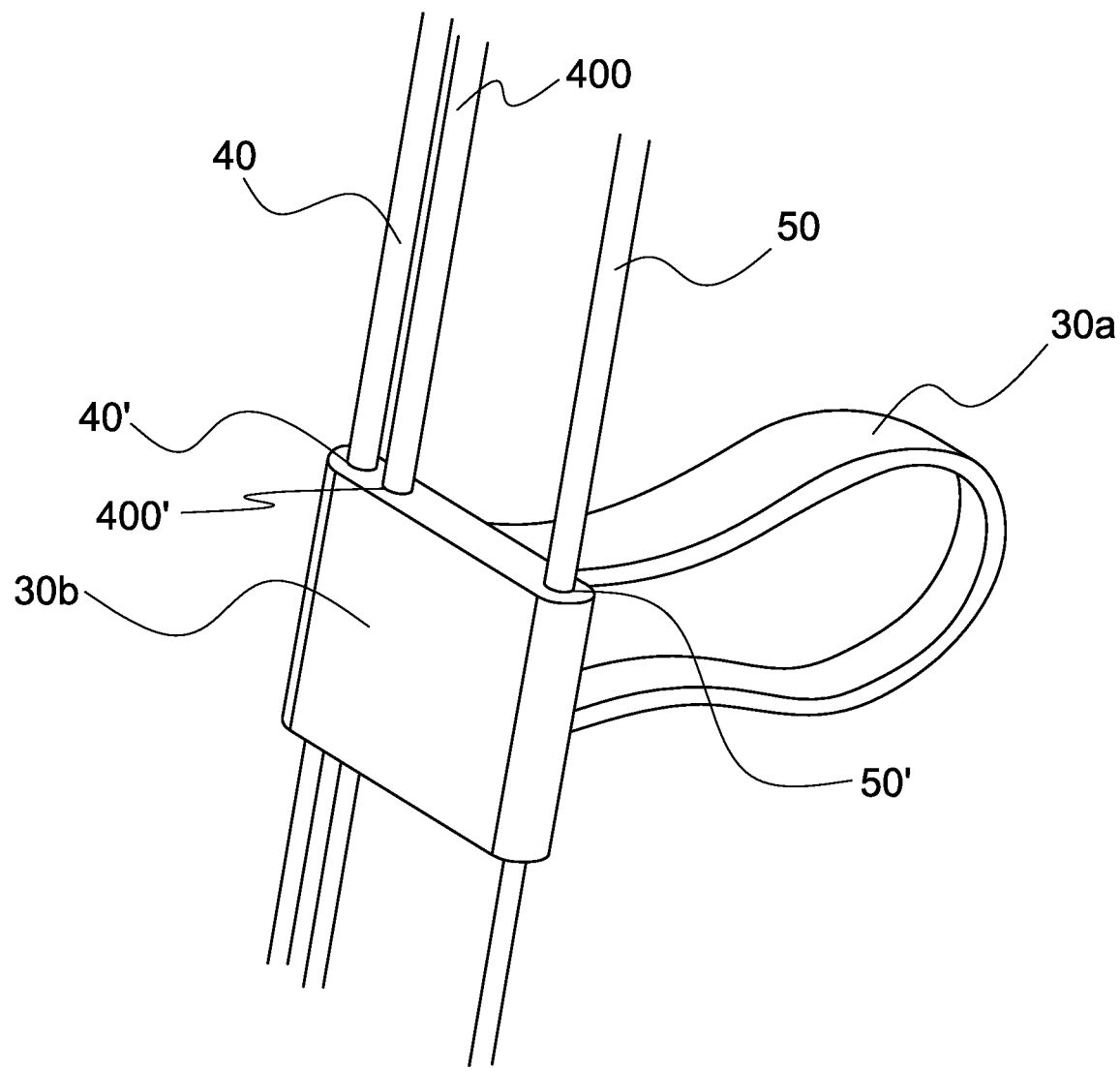
FIG. 3 shows the positioning plate and the positioning rod according to an embodiment of the present invention.
Figure 4:
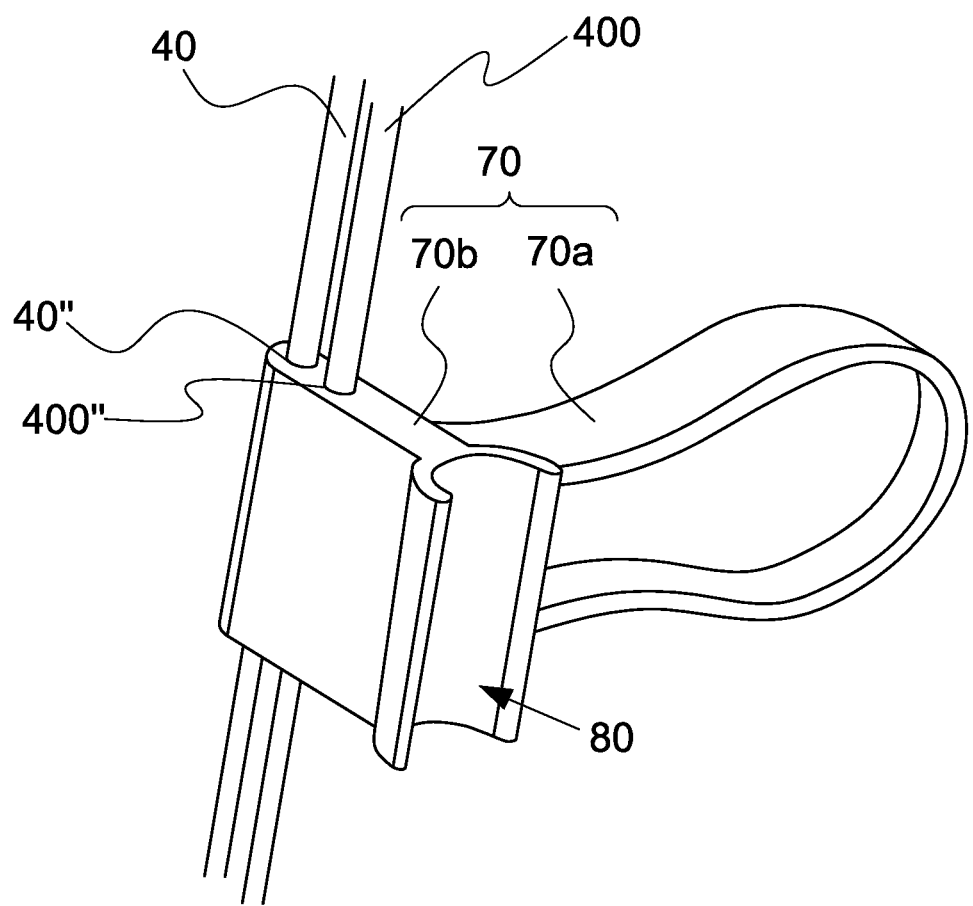
FIG. 4 shows another positioning plate and the positioning rod according to an embodiment of the present invention.

FIG. 1 shows some components of the implant guide system for hip replacement surgery according to an embodiment of the present invention. FIG. 2A shows the angle guide member according to an embodiment of the present invention. FIG. 2B shows the other side of the angle guide member of FIG. 2A. FIG. 3 shows the positioning plate and the positioning rod according to an embodiment of the present invention. FIG. 4 shows another positioning plate and the positioning rod according to an embodiment of the present invention.

First, as shown in FIG. 1, the hip replacement surgery usually involves accurately placing the acetabular cup in the acetabulum 20 of the hip bone 10 and then completing the installation of the artificial hip joint. However, before the acetabular cup is accurately placed in the acetabulum 20, for the steps of grinding the surface of the acetabulum and placing the acetabular cup in the acetabulum to be performed at a precise position and angle, it is required for the precise positioning at the beginning of the operation.

As shown in FIG. 1, the implant guide system for hip replacement surgery according to an embodiment of the present invention comprises an angle guide member 60, a first positioning plate 30, a first positioning rod 50, a second positioning rod 40, and a third positioning rod 400. As shown in FIG. 1 and FIG. 3, the first positioning plate 30 is composed of a first holding portion 30a and a first spacing portion 30b. The first spacing portion 30b has a second through hole 50', a third through hole 40' and a fourth through hole 400' that are parallel to each other. The second through hole 50' and the third through hole 40' are disposed at the opposing sides of the first positioning plate 30. The fourth through hole 400' is adjacent to the third through hole 40'.

In this embodiment, the width of the first spacing portion 30b is 45 mm. In another embodiment, the width of the first spacing portion 30b is 55 mm. In other embodiments, the width of the first spacing portion 30b is between 30 mm and 70 mm. In other embodiments, the width of the first spacing portion 30b is between 40 mm and 60 mm. The width of the first spacing portion 30b refers to the distance from the center of the second through hole 50' to the center of the third through hole 40'.

As shown in FIG. 1, FIG. 2A and FIG. 2B, the angle guide member 60 is designed and manufactured by computer simulation before hip replacement surgery based on the relevant physiological information of the patient who is to undergo hip replacement surgery, so as to correspond to the surface of the patient's acetabulum 20 to be operated. As shown in FIG. 2A, the angle guide member 60 has a body 60a and a protrusion 60b that are substantially connected to each other. As shown in FIG. 1, FIG. 2A and FIG. 2B, the body 60a has a curved surface corresponding in shape to the surface of the acetabulum 20. The protrusion 60b has a first through hole 60c extending to the body 60a. An acute angle θ is defined between the virtual extension line L1 of the first through hole 60c and the flat surface of the body 60a. The flat surface is the surface where the body 60a and the protrusion 60b are connected, and is parallel to a virtual line L2. The acute angle θ is also defined between the virtual extension line L1 of the first through hole 60c and the virtual line L2.

In this embodiment, the acute angle θ between the virtual extension line L1 of the first through hole 60c and the flat surface of the body 60a is greater than 60 degrees and less than 90 degrees. In other embodiments, the acute angle θ is greater than 0 degrees and less than 90 degrees.

As shown in FIG. 1, FIG. 2A and FIG. 3, the first positioning rod 50 is inserted through the first through hole 60c of the angle guide member 60 and the second through hole 50' of the first positioning plate 30. The second positioning rod 40 is inserted through the third through hole 40' of the first positioning plate 30 and secured to a first positioning point near the acetabulum 20. The second positioning rod 40 is arranged at an acute angle relative to the flat surface of the body 60a of the angle guide member 60. In addition, the third positioning rod 400 is inserted through the fourth through hole 400' of the first positioning plate 30 and secured to a second positioning point next to the first positioning point. The third positioning rod 400 is arranged at an acute angle relative to the flat surface of the body 60a of the angle guide member 60. It should be particularly noted that the second positioning rod 40 and the third positioning rod 400 serve as references for the positioning of related instruments, tools or components from the subsequent steps to the completion of the operation.

In addition, referring to FIG. 4, the implant guide system for hip replacement surgery according to an embodiment of the present invention further comprises a second positioning plate 70. The second positioning plate 70 has a second holding portion 70a and a second spacing portion 70b that are substantially connected to each other. The second spacing portion 70b has a fifth through hole 40", a sixth through hole 400", and a first groove 80. The fifth through hole 40", the sixth through hole 400" and the first groove 80 are parallel to each other, and are disposed at the opposing sides of the second spacing portion 70b. The sixth through hole 400" is adjacent to the fifth through hole 40". The fifth through hole 40" allows the second positioning rod 40 to pass through. The sixth through hole 400" allows the third positioning rod 400 to pass through. A grinding drill is placed against the first groove 80 for grinding the surface of the acetabulum 20. In this embodiment, the size or diameter of the first groove 80 is determined according to the diameter of the matched grinding drill. That is, the diameter of part of the grinding drill leaning against the first groove 80 determines the diameter of the first groove 80.

In other embodiments, another third positioning plate (not shown in the figure) similar to the second positioning plate 70 is provided. The third positioning plate also has a groove similar to the first groove 80, which allows an acetabular cup implanter to lean against the groove for placing an acetabular cup into the acetabulum 20. However, the diameter of the groove is determined by the diameter of a device, such as an acetabular cup implanter. That is to say, the diameter of part of the acetabular cup implanter that rests on the groove of the third positioning plate determines the diameter of the groove.

In this embodiment, the width of each of the first spacing portion 30b and the second spacing portion 70b is 45 mm. In another embodiment, the width of each of the first spacing portion 30b and the second spacing portion 70b is 55 mm. In other embodiments, the width of each of the first spacing portion 30b and the second spacing portion 70b is between 30 mm and 70 mm. In other embodiments, the width of each of the first spacing portion 30b and the second spacing portion 70b is between 40 mm and 60 mm. The width of the second spacing portion 70b refers to the distance from the center of the fifth through hole 40" to the center of the first groove 80. In addition, the width and definition of the spacing portion of the third positioning plate are the same as those of the second spacing portion 70b, and will not be repeated hereinafter.

FIGS. 5-14 are schematic views, illustrating the operation of the implant guide system for hip replacement surgery according to an embodiment of the present invention.

Figure 5:
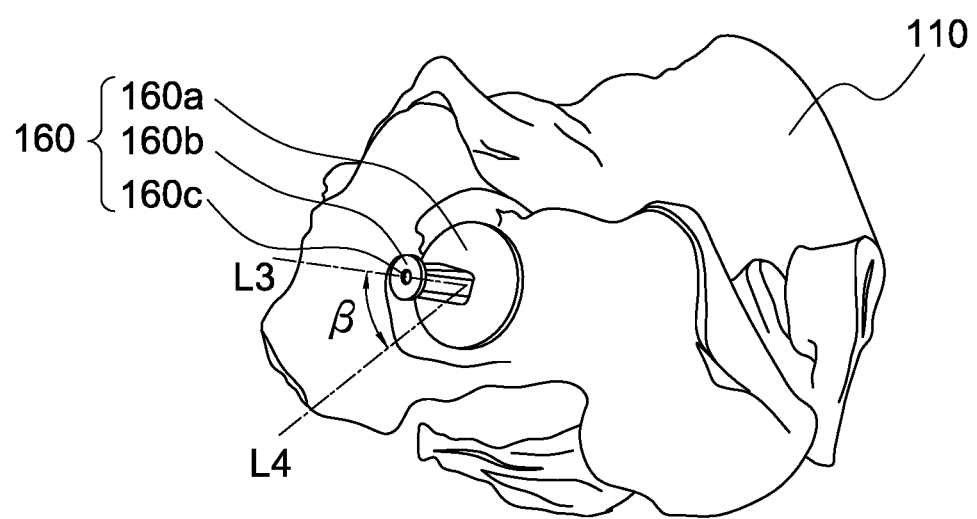
FIGS. 5-14 are schematic views, illustrating the operation of the implant guide system for hip replacement surgery according to an embodiment of the present invention.

First, as shown in FIG. 5, an angle guide member 160 is placed in the acetabulum 6 (referring to FIG. 9) of the hip bone 110. The angle guide member 160 is composed of a body 160a and a protrusion 160b. The body 160a and the protrusion 160b are substantially connected to each other. Similarly, the angle guide member 160 is designed and manufactured by computer simulation before hip replacement surgery based on the relevant physiological information of the patient who is to undergo hip replacement surgery, so as to correspond to the surface of the patient's acetabulum to be operated. Thus, the body 160a has a curved surface corresponding in shape to the surface of the acetabulum. The protrusion 160b has a first through hole 160c extending to the body 160a. An acute angle β is defined between the virtual extension line L3 of the first through hole 160c and the flat surface of the body 160a. The flat surface is the surface where the body 160a and the protrusion 160b are connected, and is parallel to a virtual line L4. The acute angle θ is also defined between the virtual extension line L3 of the first through hole 160c and the virtual line L4.

Figure 6:
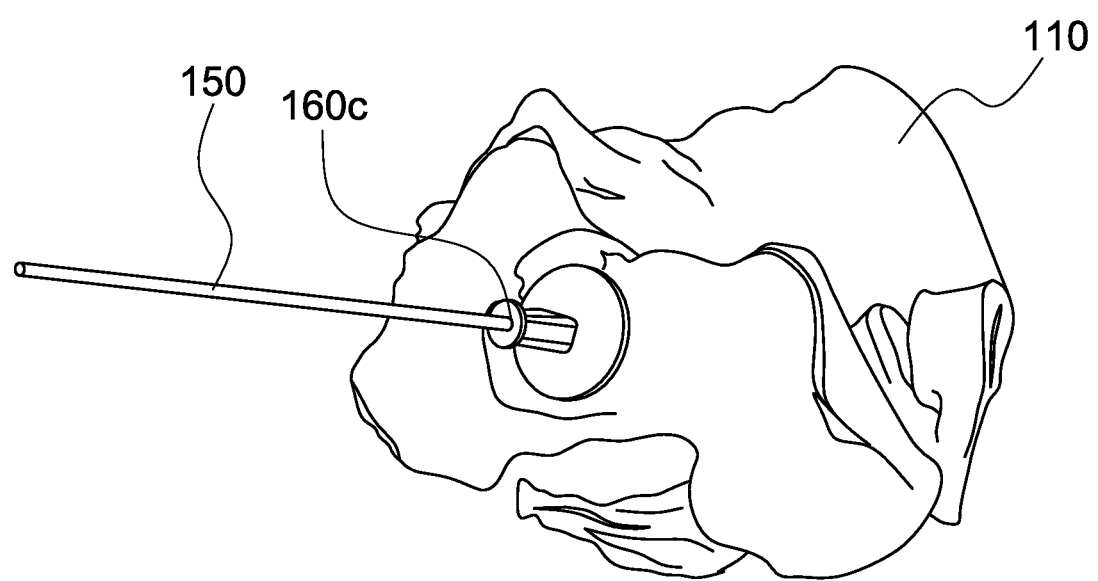

Next, as shown in FIG. 6, a first positioning rod 150 is inserted into the first through hole 160c of the angle guide member 160. In this embodiment, the diameter of the first positioning rod 150 is 3 mm.

Figure 7:
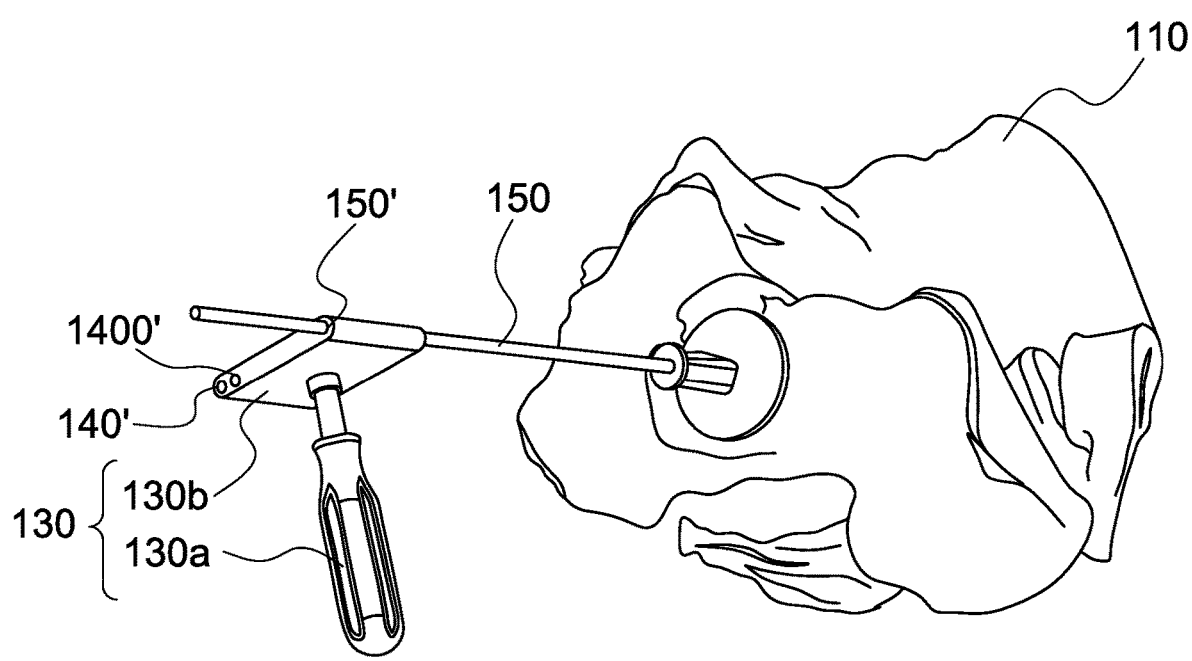

Then, as shown in FIG. 7, a first positioning plate 130 is coupled to the first positioning rod 150. The first positioning plate 130 is composed of a first holding portion 130a and a first spacing portion 130b. The first spacing portion 130b has a second through hole 150', a third through hole 140' and a fourth through hole 1400' that are parallel to each other. The second through hole 150' and the third through hole 140' are disposed at the opposing sides of the first positioning plate 130. The fourth through hole 1400' is adjacent to the third through hole 140'. The first positioning rod 150 is inserted through the second through hole 150' of the first spacing portion 130b. In this embodiment, the width of the first spacing portion 130b is 45 mm. In another embodiment, the width of the first spacing portion 130b is 55 mm. In other embodiments, the width of the first spacing portion 130b is between 30 mm and 70 mm. In other embodiments, the width of the first spacing portion 130b is between 40 mm and 60 mm. The width of the first spacing portion 130b refers to the distance from the center of the second through hole 150' to the center of the third through hole 140'.

Figure 8:
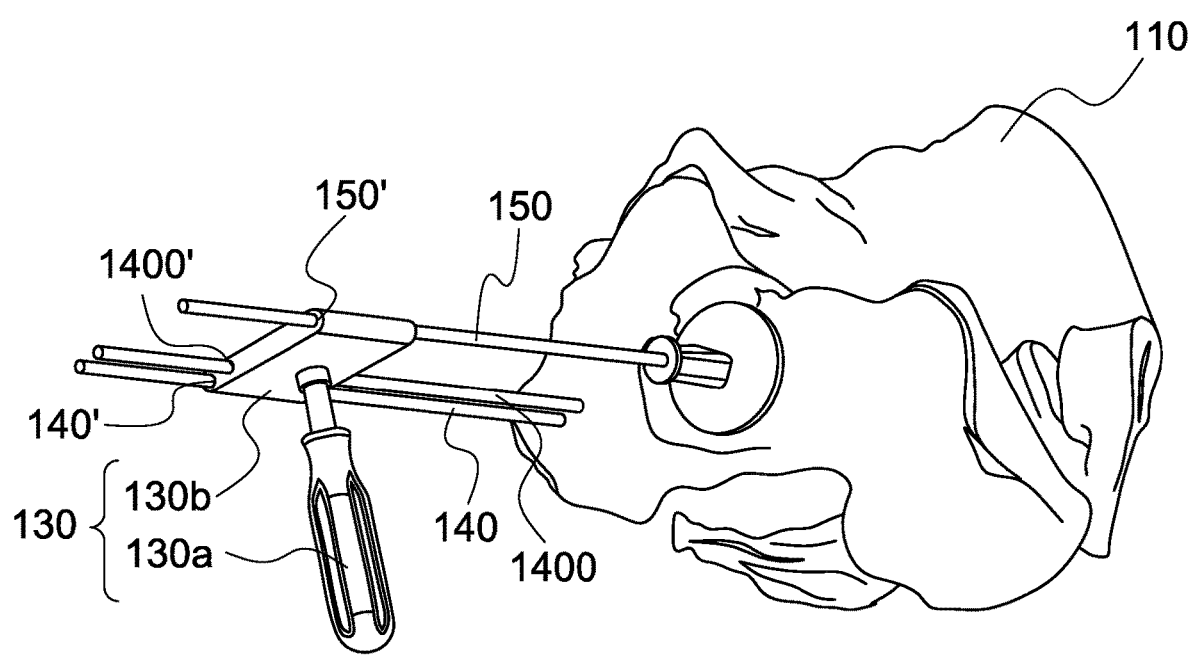

After that, as shown in FIG. 8, the second positioning rod 140 and the third positioning rod 1400 are coupled to the first positioning plate 130. The second positioning rod 140 is inserted through the third through hole 140' of the first spacing portion 130b and secured near the acetabulum, serving as a first positioning point. In addition, the third positioning rod 1400 is inserted through the fourth through hole 1400' of the first positioning plate 130 and secured to a second positioning point next to the first positioning point. The second positioning rod 140 and the third positioning rod 1400 are secured at the respective positioning points, and serve as references for the positioning of related instruments, tools or components from the subsequent steps to the completion of the operation. In this embodiment, the diameter of each of the second positioning rod 140 and the third positioning rod 1400 is 3 mm. Similarly, in this embodiment, the second positioning rod 140 and the third positioning rod 1400 that are parallel to each other are arranged at an acute angle relative to the flat surface of the body 160a of the angle guide member 160. The definition of this acute angle can refer to the foregoing, and the acute angle is greater than 60 degrees but less than 90 degrees. In other embodiments, the acute angle is greater than 0 degrees and less than 90 degrees.

Figure 9:
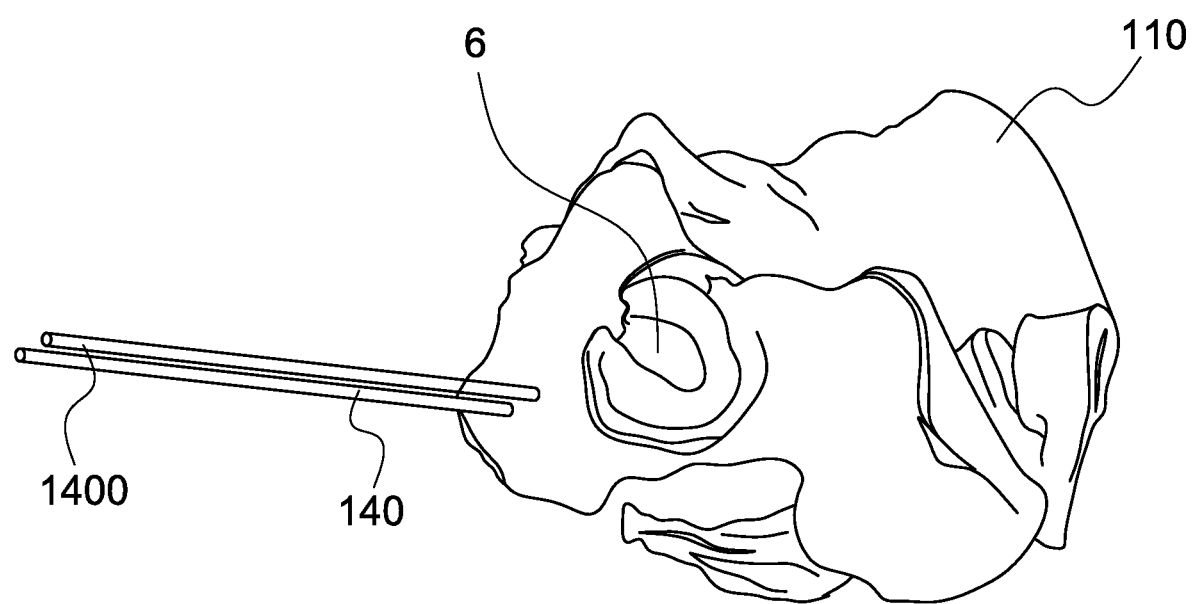

Next, as shown in FIG. 9, the first positioning plate 130, the first positioning rod 150 and the angle guide member 160 are removed, leaving only the second positioning rod 140 and the third positioning rod 1400. In addition, after the angle guide member 160 is removed, the surface of the acetabulum 6 is exposed.

Figure 10:
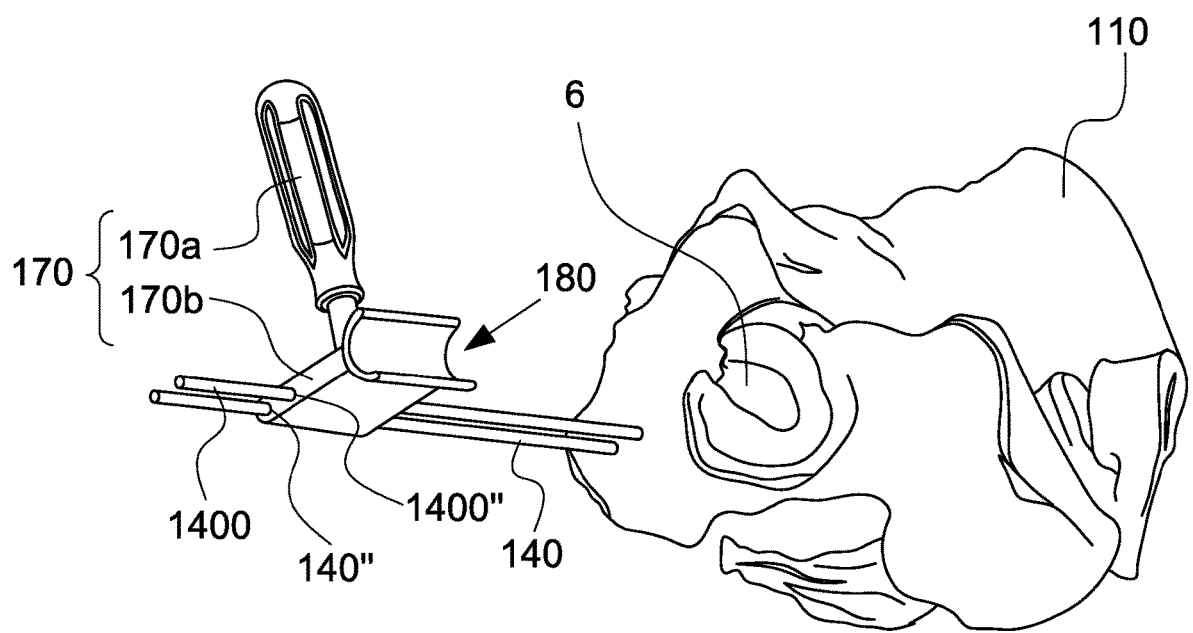
Figure 11:
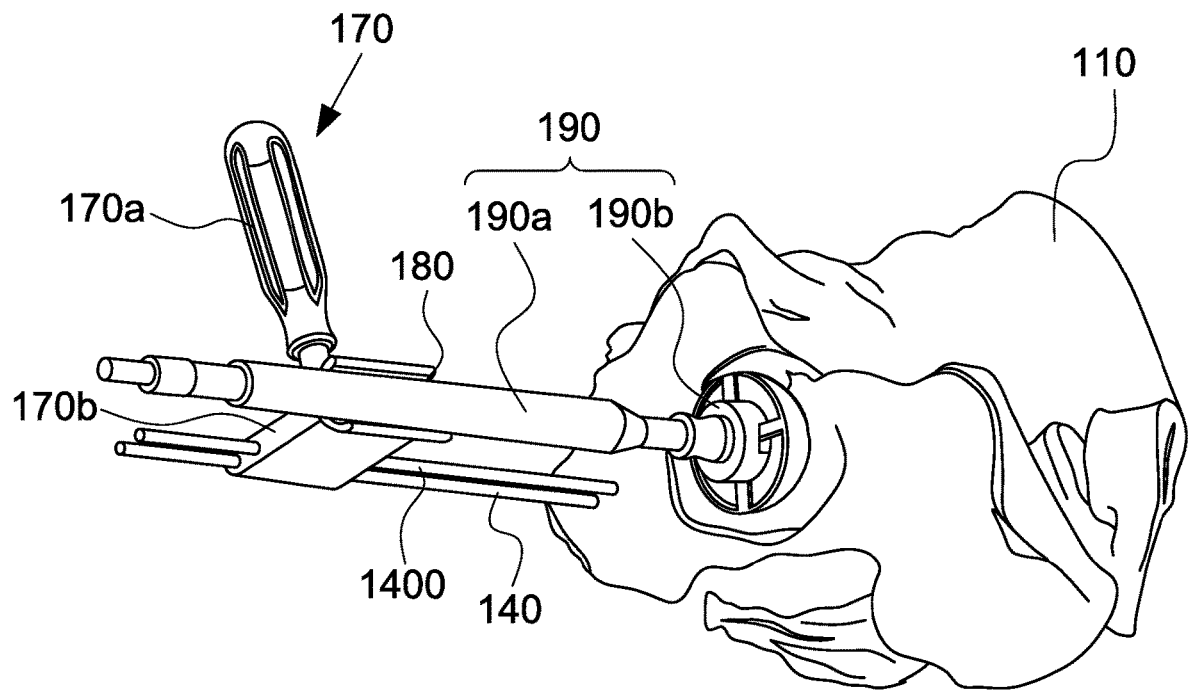

Then, as shown in FIG. 10, a second positioning plate 170 is coupled to the second positioning rod 140 and the third positioning rod 1400. The second positioning plate 170 has a second holding portion 170a and a second spacing portion 170b that are substantially connected to each other. The second spacing portion 170b has a fifth through hole 140", a sixth through hole 1400", and a first groove 180. The fifth through hole 140" and the first groove 180 are parallel to each other, and are disposed at the opposing sides of the second spacing portion 170b. The sixth through hole 1400" is adjacent to the fifth through hole 140". The fifth through hole 140" allows the second positioning rod 140 to pass through. The sixth through hole 1400" allows the third positioning rod 1400 to pass through. A grinding drill 190 as shown in FIG. 11 is placed against the first groove 180 for grinding the surface of the acetabulum 60. In this embodiment, the width of the second spacing portion 170b is 45 mm. In another embodiment, the width of the second spacing portion 170b is 55 mm. In other embodiments, the width of the second spacing portion 170b is between 30 mm and 70 mm. In other embodiments, the width of the second spacing portion 170b is between 40 mm and 60 mm. The width of the second spacing portion 170b refers to the distance from the center of the fifth through hole 140" to the center of the first groove 180.

As shown in FIG. 11, a grinding drill 190 is placed against the first groove 180 of the second spacing portion 170b for grinding the surface of the acetabulum 6. The grinding drill 190 has a holding portion 190a and a drill bit 190b. The drill bit 190b is configured to grind the surface of the acetabulum 6.

Figure 12:
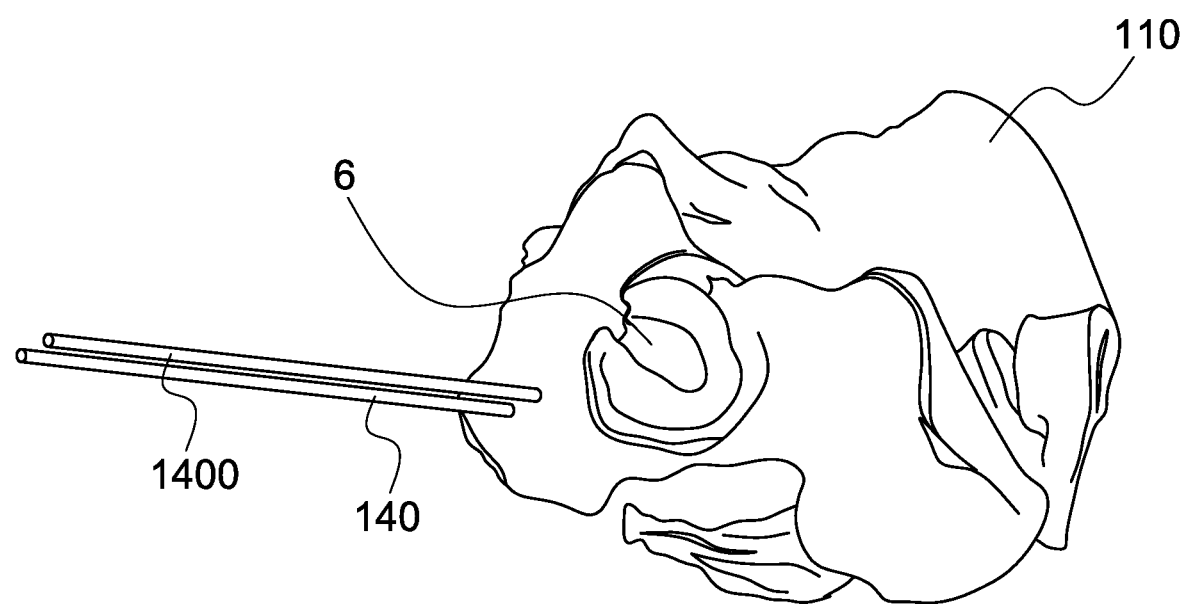

Next, as shown in FIG. 12, after the grinding of the surface of the acetabulum 6 is completed, the second positioning plate 170 and the grinding drill 190 are removed, leaving only the second positioning rod 140 and the third positioning rod 1400.

Figure 13:
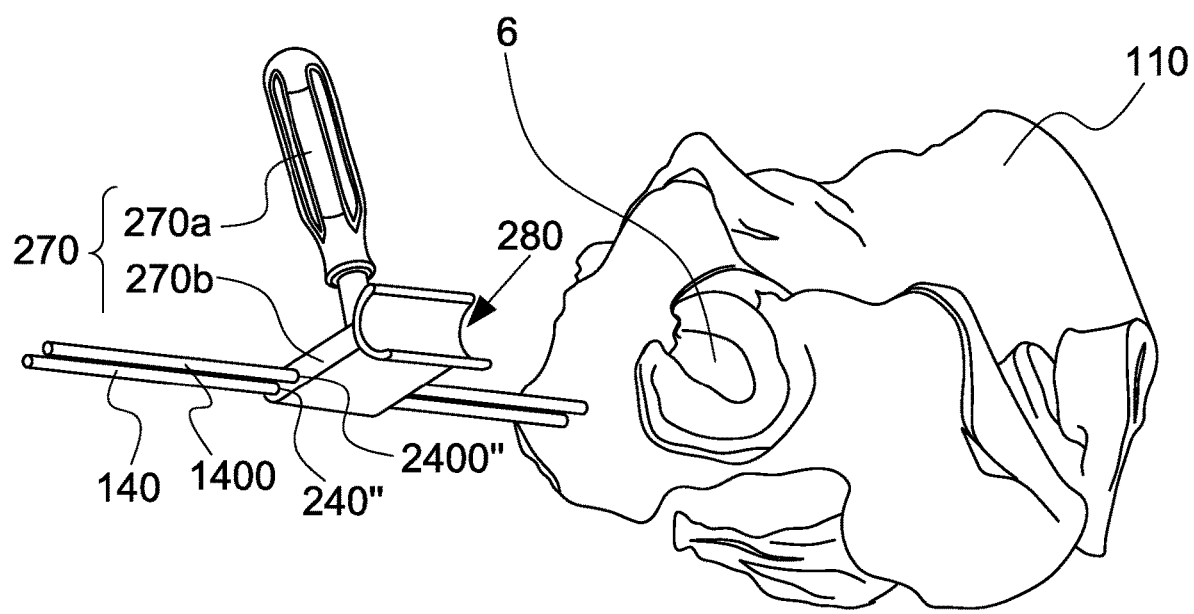
Figure 14:
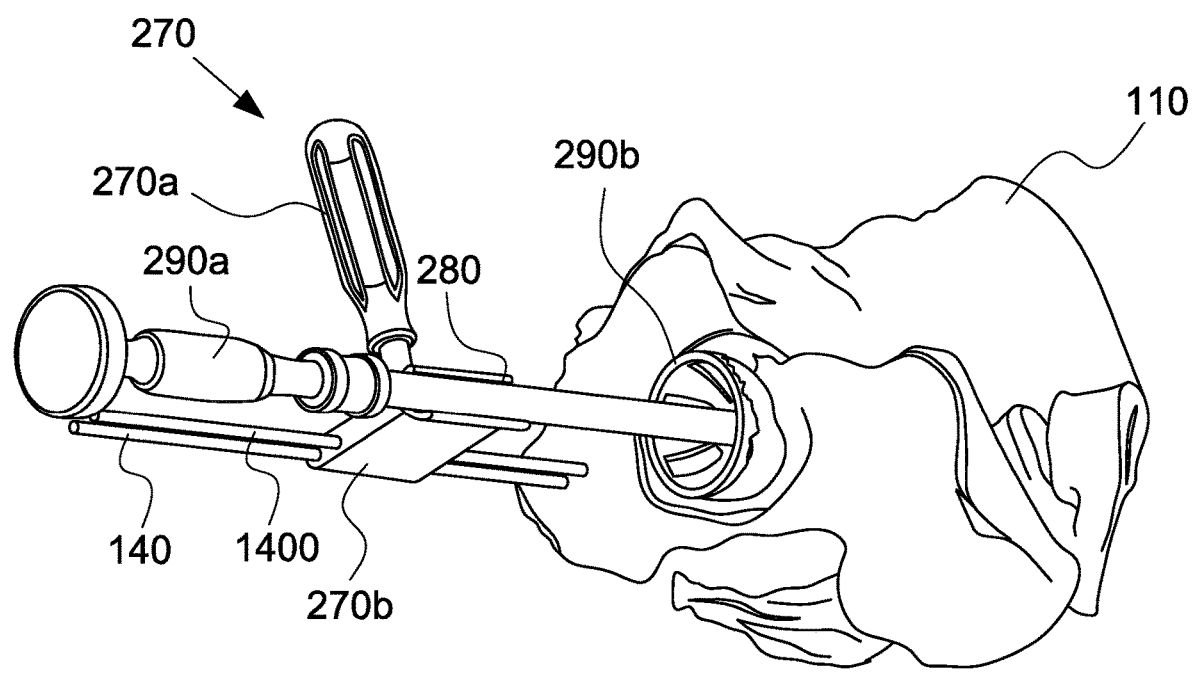

Then, as shown in FIG. 13, a third positioning plate 270 is coupled to the second positioning rod 140 and the third positioning rod 1400. The third positioning plate 270 has a third holding portion 270a and a third spacing portion 270b that are substantially connected to each other. The third spacing portion 270b has a seventh through hole 240", an eighth through hole 2400", and a second groove 280. The seventh through hole 240", the eighth through hole 2400" and the second groove 280 are parallel to each other, and are disposed at the opposing sides of the third spacing portion 270b. The eighth through hole 2400" is adjacent to the seventh through hole 240". The seventh through hole 240" allows the second positioning rod 140 to pass through. The eighth through hole 2400" allows the third positioning rod 1400 to pass through. As shown in FIG. 14, an acetabular cup implanter 290a is placed against the second groove 280, so that the acetabular cup 290b is accurately placed into the acetabulum 6. In this embodiment, the width of the third spacing portion 270b is 45 mm. In another embodiment, the width of the third spacing portion 270b is 55 mm. In other embodiments, the width of the third spacing portion 270b is between 30 mm and 70 mm. In other embodiments, the width of the third spacing portion 270b is between 40 mm and 60 mm. The width of the third spacing portion 270b refers to the distance from the center of the seventh through hole 240" to the center of the second groove 280. In the embodiment of the present invention, the diameters of the second groove 280 and the first groove 180 are different, and the diameter of the second groove 280 is less than the diameter of the first groove 180.

In the embodiment of the present invention, the first spacing portion 70b of the first positioning plate 70, the second spacing portion 170b of the second positioning plate 170 and the third spacing portion 270b of the third positioning plate 270 have the same width.

Then, as shown in FIG. 14, the acetabular cup implanter 290a is placed against the second groove 280 of the third spacing portion 270b, and the acetabular cup 290b is accurately coupled to the acetabulum.

In the embodiments of the present invention, the first positioning rod 150 and the second positioning rod 140 may be k-pins.

Although particular embodiments of the present invention have been described in detail for purposes of illustration, various modifications and enhancements may be made without departing from the spirit and scope of the present invention. Accordingly, the present invention is not to be limited except as by the appended claims.

What is claimed is:

1. An implant guide system for hip replacement surgery, comprising:
   an angle guide member, having a body and a protrusion extending from the body, the body having a curved surface corresponding in shape to a surface of a patient's acetabulum, the protrusion having a first through hole extending to the body, an acute angle being defined between a virtual extension line of the first through hole and a flat surface of the body; and
   a first positioning plate, having a first holding portion and a first spacing portion extending from the first holding portion, the first spacing portion having a second through hole, a third through hole and a fourth through hole that are parallel to each other; a first positioning rod being inserted through the first through hole and the second through hole, a second positioning rod being inserted through the third through hole and secured to a first positioning point near the acetabulum, a third positioning rod being inserted through the fourth through hole and secured to a second positioning point next to the first positioning point, the second positioning rod and the third positioning rod being arranged at the acute angle relative to the flat surface of the body so that an acetabular cup can be accurately coupled to the acetabulum.

2. The implant guide system for hip replacement surgery as claimed in claim 1, further comprising:
  a second positioning plate, having a second holding portion and a second spacing portion extending from the second holding portion, the second spacing portion having a fifth through hole, a sixth through hole and a first groove, wherein after the first positioning plate, the first positioning rod and the angle guide member are removed, the second positioning rod is inserted through the fifth through hole, and the third positioning rod is inserted through the sixth through hole, and a grinding drill is placed against the first groove for grinding the surface of the acetabulum; and
  a third positioning plate, having a third holding portion and a third spacing portion extending from the third holding portion, the third spacing portion having a seventh through hole, an eighth through hole and a second groove, wherein after the second positioning plate and the grinding drill are removed, the second positioning rod is inserted through the seventh through hole, and the third positioning rod is inserted through the eighth through hole, and an acetabular cup implanter is placed against the second groove so that the acetabular cup is accurately coupled to the acetabulum;
  the first spacing portion, the second spacing portion and the third spacing portion having a same width.

3. The implant guide system for hip replacement surgery as claimed in claim 2, wherein the width of each of the first spacing portion, the second spacing portion and the third spacing portion is between 30 mm and 70 mm.

4. The implant guide system for hip replacement surgery as claimed in claim 2, wherein the width of each of the first spacing portion, the second spacing portion and the third spacing portion is 45 mm.

5. The implant guide system for hip replacement surgery as claimed in claim 2, wherein the width of each of the first spacing portion, the second spacing portion and the third spacing portion is 55 mm.

6. The implant guide system for hip replacement surgery as claimed in claim 2, wherein the width of the first spacing portion is the distance from a center of the second through hole to a center of the third through hole.

7. The implant guide system for hip replacement surgery as claimed in claim 2, wherein the width of the second spacing portion is the distance from a center of the fifth through hole to a center of the first groove, and the width of the third spacing portion is the distance from a center of the seventh through hole to a center of the second groove.

8. The implant guide system for hip replacement surgery as claimed in claim 1, wherein the angle guide member is customized, and the acute angle and the curved surface of the angle guide member are determined based on the patient's physiological information before hip replacement surgery.

9. The implant guide system for hip replacement surgery as claimed in claim 1, wherein the acute angle between the virtual extension line of the first through hole and the flat surface of the body is greater than 0 degrees and less than 90 degrees.

10. The implant guide system for hip replacement surgery as claimed in claim 1, wherein the acute angle between the virtual extension line of the first through hole and the flat surface of the body is greater than 60 degrees and less than 90 degrees.

* * * * *